United States Patent [19]

Yokoyama

[11] Patent Number: 4,803,013

[45] Date of Patent: Feb. 7, 1989

[54] HALOGENATED NAPHTHALENE DERIVATIVES

[75] Inventor: Nobuo Yokoyama, Musashino, Japan

[73] Assignee: Nippon Oil Co., Ltd., Tokyo, Japan

[21] Appl. No.: 169,221

[22] Filed: Mar. 16, 1988

[30] Foreign Application Priority Data

Mar. 17, 1987 [JP] Japan .................................. 62-61788
Mar. 17, 1987 [JP] Japan .................................. 62-61789

[51] Int. Cl.[4] ............................................ H01B 3/24
[52] U.S. Cl. .................................. 252/580; 568/322; 568/323; 568/328
[58] Field of Search ................ 252/580; 568/322, 323, 568/328

*Primary Examiner*—Robert A. Wax
*Attorney, Agent, or Firm*—Bruce L. Adams; Van C. Wilks

[57] ABSTRACT

Novel halogenated naphthalene derivatives of the formula

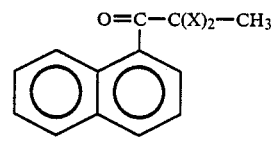

where X is F or Br, and a process for making the same are disclosed. Insulating oils are also disclosed which essentially comprise such a fluorine-containing compound and commonly used hydrocarbon insulating oils. The additive is highly conductive to improved dielectric constant, dielectric loss, hydrogen gas absorptivity, fluidity and viscosity characteristics.

14 Claims, 4 Drawing Sheets

2,2-DIBROMO-1-(1-NAPHTHYL)-1-PROPANONE 2,2-DIFLUORO-1-(1-NAPHTHYL)-1-PROPANONE

HALOGENATED NAPHTHALENE DERIVATIVES

BACKGROUND OF THE INVENTION

1. Field of the Invention:

This invention relates to halogenated naphthalene derivatives and a process for their production and further to insulating oils containing such derivatives.

2. Description of the Prior Art:

Insulating oils are known in common use for condensers, which oils are predominantly of aromatic hydrocarbons. Attempts have been made to reduce the size of condensers with use of a variety of synthetically derived oils of high dielectric or polarity but with little or no success. Such prior synthetic oils are too dielectrically dissipative, physicochemically inadequate and insufficiently insulative.

SUMMARY OF THE INVENTION

The present invention is based on the discovery that a selected class of halogenated naphthalene derivatives when combined with certain hydrocarbon oils can contribute to enhanced insulation characteristics.

It is the primary object of the invention to provide novel naphthalene derivatives having two fluorine or bromine atoms chemically attached to one selected position, a process for producing these derivatives and also insulating oils containing such a fluorine-containing compound. The insulating oils according to the invention excel in dielectric constant ($\epsilon$), dielectric loss (tan $\delta$), hydrogen gas absorptivity, fluidity and viscosity stability at low temperature.

In the practice of the invention, a brominated naphthalene derivative acts as an intermediate in producing a fluorinated derivative. Both compounds are also applicable as feedstock or intermediates to pharmaceutical products, agricultural chemicals and photosensitive materials.

To attain this and other objects and advantages of the invention, as will be better understood from the following detailed description, there is provided a naphthalene derivative of the formula

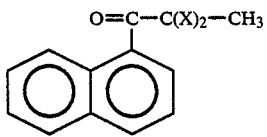

where X is a fluorine or bromine atom.

In another embodiment of the invention there is provided a process for producing a naphthalene derivative of the formula

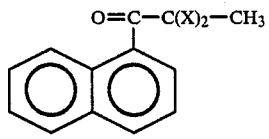

where X is a fluorine or bromine atom, which comprises (a) preparing a mixture of 1-(1-naphthyl)-1-propanone and 1-(2-naphthyl)-1-propanone by reaction of naphthalene with propionyl chloride at from 20° to 250° C. and in the presence of a Friedel-Crafts catalyst, (b) reacting compound (a) with a brominating agent at from 0° to 80° C. and with or without use of a solvent, thereby giving 2,2-dibromo-1-(1-naphthyl)-1-propanone combined with 2,2-dibromo-1-2-naphthyl)-1-propanone, and (c) subsequently purifying and isolating compound (b) with use of a solvent, whereby 2,2-dibromo-1-(1-naphthyl)-1-propanone is provided.

In a still another embodiment of the invention there is provided an insulating oil which comprises a base oil and a fluorinated naphthalene derivative.

DETAILED DESCRIPTION OF THE INVENTION

Figure 1:
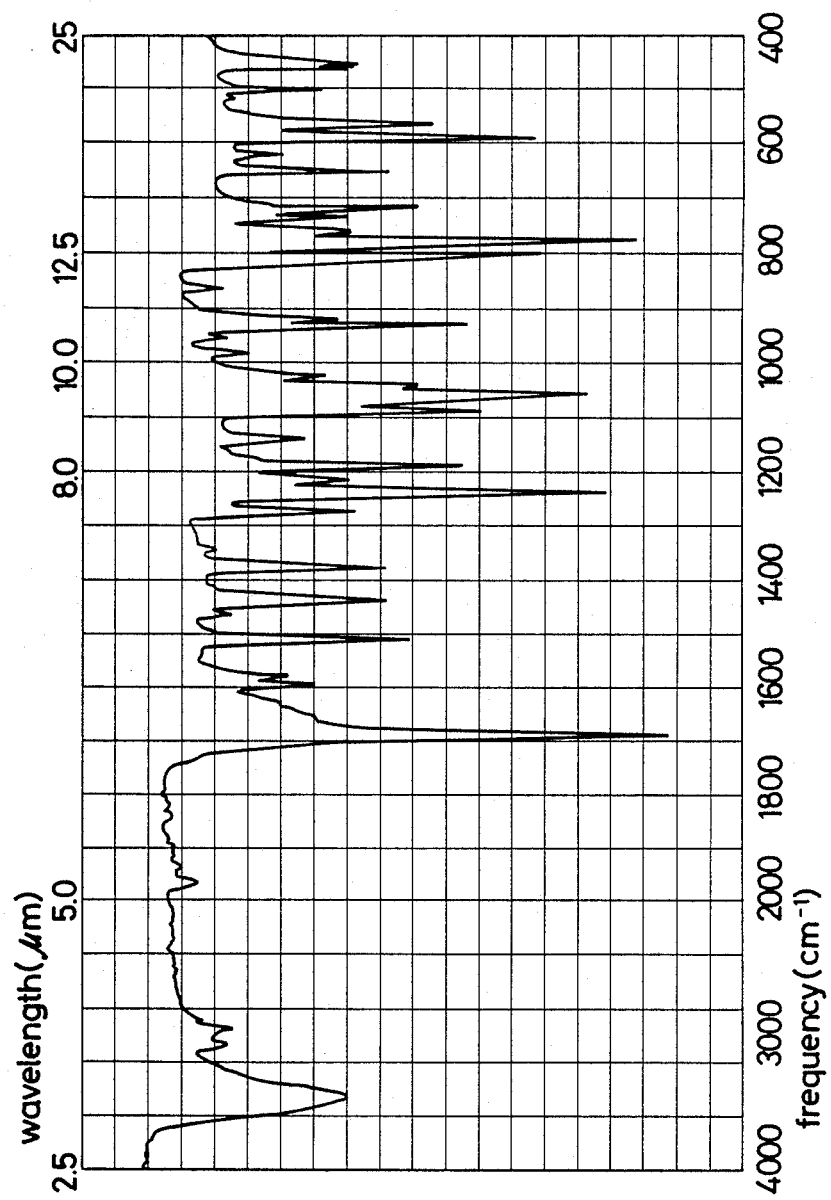
FIGS. 1 through 4 are IR and $^{13}$C-NMR spectral diagrams of the brominated and fluorinated compounds provided in accordance with the present invention.

Compounds contemplated under the present invention are halogen-containing naphthalene derivatives of the formula

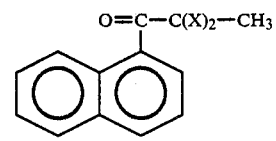

where X is a fluorine or bromine atom.

Specific examples of such compounds include 2,2-difluoro-1-(1-naphthyl)-1-propanone and 2,2-dibromo-1-(1-naphthyl)-1-propanone represented by the formulae (I) and (II), respectively:

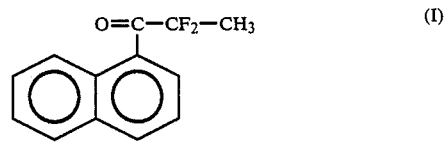

and

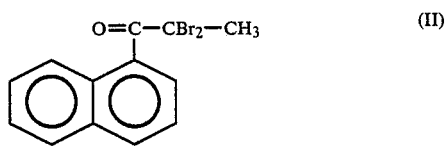

Compound (I), a fluorine-containing derivative, is obtainable for example by brominating a given composite naphthylpropanone derived from the Friedel-Crafts reaction, followed by recrystallization, and subsequently by fluorinating the resultant compound and purifying the final product. The intermediate product is compound (II), a bromine-containing derivative.

More specifically, 1-(1-naphthyl)-1-propanone combined with 1-(2-naphthyl)-1-propanone is useful as a starting material which is readily available for instance from the reaction of naphthalene with propionyl chloride at a temperature of 20° to 250° C. and in the presence of a known Friedel-Crafts catalyst such as aluminum chloride or iron chloride. The starting material is allowed to react with a brominating agent at from 0° to 80° C. and if necessary with use of a solvent to thereby substitute Br$_2$ for H at the 2-position of the composite naphthylpropanone, whereby a mixture of 2,2-dibromo-1-(1-naphthyl)-1-propanone and 2,2-dibromo-1-(2-naphthyl)-1-propanone is provided to a highly selective extent. Suitable brominating agents include numerous compounds commonly employed for bromination, among which gaseous bromine and N-bromosuccinimide are particularly preferred. Solvents where desired may be selected for example from carbon tetrachloride, chloroform, dichloroethane, tetrahydrofuran, carbon disulfide and the like.

The crude product thus brominated is purified by dissolving in a solvent at a temperature higher than room temperature, followed by cooling to about 0° C. or lower temperature, with the result that 2,2-dibromo-1-(1-naphthyl)-1-propanone, i.e. compound (II), is separated in the form of crystals from 2,2-dibromo-1-(2-naphthyl)1-propanone and limited amounts of monobromo substituents byproduced upon bromination and held in the liquid phase. Typical examples of solvents include aliphatic hydrocarbons of 5 to 8 carbon atoms such as pentane, hexane, heptane, octane and the like, aliphatic monovalent alcohols of 1 to 4 carbon atoms such as methanol, ethanol, propanol, butanol and the like, and their combinations. Compound (II) is isolated by filtration and may be repeatedly recrystallized to further improve its purity.

Compound (II) is novel per se and important as an intermediate to produce compound (I).

Pure compound (I) may be derived by reacting compound (II) with a fluorinating agent at from 0° to 120° C. and in the presence or in the absence of a solvent, and subsequently by removing byproducts from the reaction product by distillation. No particular restriction is imposed on the kind of the fluorinating agent which however may be conveniently selected from inorganic materials such as fluorine gas, hydrogen fluoride, sulfur fluoride and metallic fluorides including potassium fluoride, xenon fluoride, mercury fluoride, silver fluoride, antimony fluoride and the like, and organic materials such as $CHF_3$, $CF_3OF$, $(C_2H_5)_2NSF_3$, $\phi_4P^+HF_2^-$, $\phi_3(iso-C_3H_7)P^+HF_2^-$ and the like. Solvents typically include carbon tetrachloride, perfluorohexane, perfluorooctane and the like.

An insulating oil according to the invention may be produced by blending a base oil with compound (I). Base oils suitable for the purpose of the invention include any known insulating oils of a mineral type and also of a synthetic type such as hard alkylbenzenes, soft alkylbenzenes, polybutenes, alkylnaphthalenes, diarylalkanes, silicone oils and the like. The amount of compound (I) to be added should be usually in the range of 5 to 40%, preferably 10 to 25% by weight based on the total weight of the oil composition. Antioxidants may also be used but in small amounts.

The following examples are given to further illustrate the invention.

EXAMPLE 1

(1) Synthesis of Composite Naphthylpropanone [1-(1-Naphthyl)-1-Propanone and 1-(2-Naphthyl)-1-Propanone]:

Solution A—51 g propionyl chloride and 77 g aluminum chloride dissolved in 160 ml dichloroethane Solution B—79 g naphthalene dissolved in 160 ml dichloroethane Solutions A and B were reacted according to the Friedel-Crafts method. To solution A taken into a flask was added with stirring solution B at 35° C. over 3 hours. The reaction mixture was combined with 35 ml dilute hydrochloric acid and then cooled to separate a white solid. After removal of the solid by filtration, the filtrate was washed with water, dried over anhydrous sodium sulfate and subsequently distilled, giving 85 g of a distillate of 143° to 146° C./4 mm Hg.

The resulting distillate was identified by GC-MS analysis as being composed of 1-(1-naphthyl)-1-propanone and 1-(2-naphthyl)-1-propanone in a 2 to 1 ratio. The purity was 98.3%.

(2) Bromination of Composite Naphthylpropanone:

Solution C—75 g bromine dissolved in 300 ml chloroform

Solution D—75 g bromine dissolved in 100 ml chloroform 85 g Composite naphthylpropanone resulting from synthesis (1) above was taken into a 1 liter flask to which solution C was added dropwise with water cooling at 18° C., followed by addition of solution D with stirring at 25° C. The system was warmed to 60°C. and stirred for another 2 hours. The reaction mixture was distilled to remove chloroform, thereby providing 148 g of a brown solid.

GC-MS analysis showed that the resulting solid was brominated naphthylpropanone composed of 58.4% 2,2-dibromo-1-(1-naphthyl)-1-propanone. 28.0% 2,2-dibromo-1-2-naphthyl)-1-propanone, 6.8% 2-bromo-1-(1-naphthyl)-1propanone and 3.3% 2-bromo-1-(2-naphthyl)-1-propanone, totalling at 96.5% by weight.

(3) Isolation of 2,2-Dibromo-1-(1-Naphthyl)-1-Propanone:

148 g Solid obtained in bromination 2) was dissolved in a mixture of 35 ml hexane and 35 ml ethanol and settled overnight at 0° C. to crystallize. After this treatment was repeated three times, the solvent was removed by distillation to obtain 92 g of a crystalline product.

Figure 2:
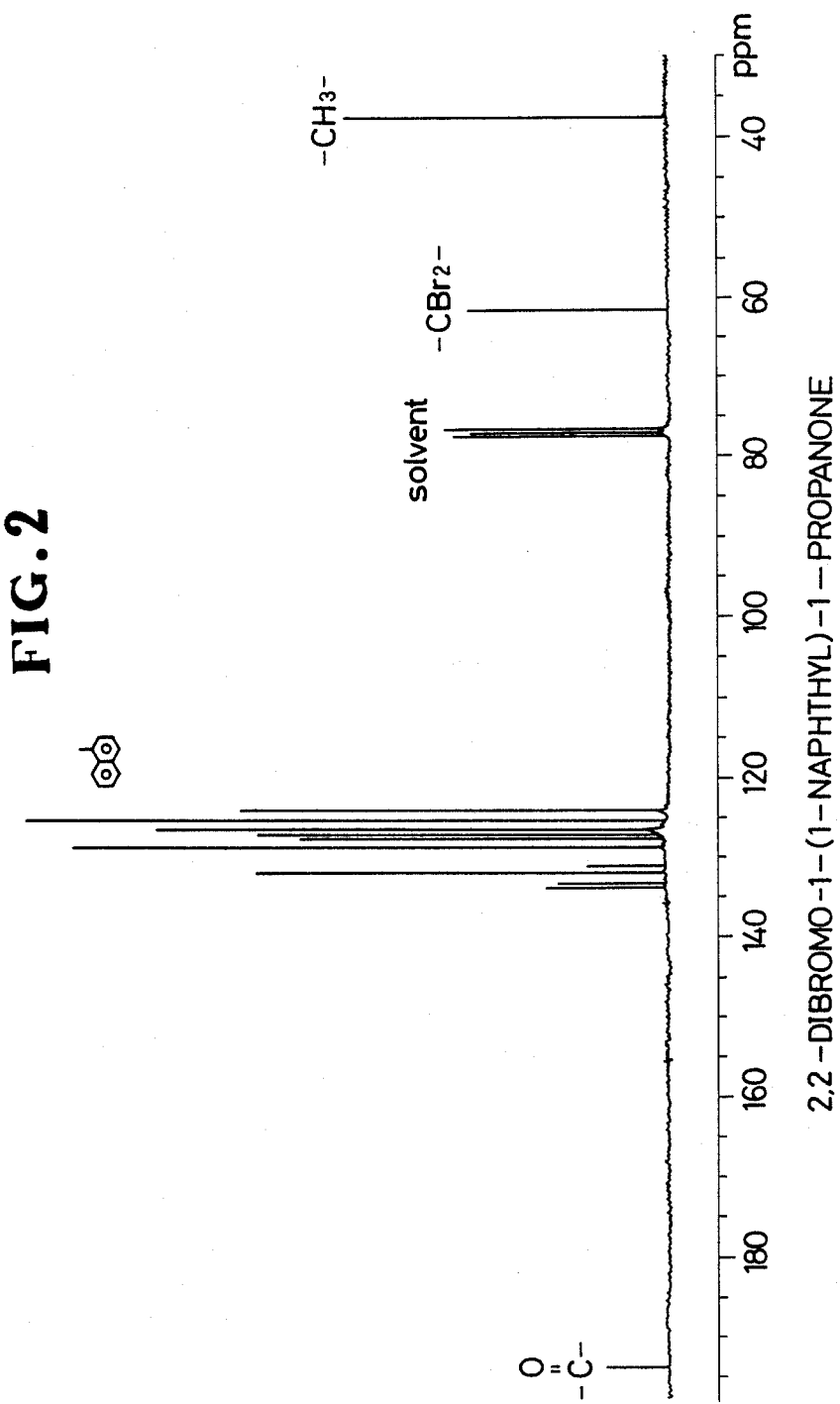

The resulting product was examined for GC-MS, IR and $^{13}C$-NMR, the latter two spectra being shown in FIGS. 1 and 2. It was identified as 98.7% pure 2,2-dibromo-1(1-naphthyl)-1-propanone according to the invention.

EXAMPLE 2

In a 100 ml flask were placed 35 g crystalline brominated naphthylpropanone provided in Example 1 and 25 g mercury fluoride powder, followed by heating of the system with stirring in nitrogen atmosphere. The mixture when heated to 75° C. started to melt with mild heat evolution, and reaction took place accompanying some volatile matter vaporizing out of the flask. Heating was discontinued at 95° C. Subsequently, 100 ml carbon tetrachloride was poured into the reaction mixture from which solid matter was then separated with a filter paper. On removal of the solvent by distillation, the residue was fractionated to obtain 7 g of a light yellow distillate of 110°C./3 mm Hg.

The resulting distillate showed a purity of 96% by GC examination. The results of eemental analysis and the theoretical values for 2,2-difluoro-1-(1-naphthyl)-1propanone were given below. Fluorine (F) was determined by potentiometrically titrating an aqueous solution in which combustion gas of the distillate had been absorbed. Oxygen (0) was undeterminable due to the interference of F.

|  | C | H | F |
|---|---|---|---|
| Empirical: | 71.3 | 4.71 | 16.9 |
| Theoretical: | 70.9 | 4.55 | 17.3 |

-continued

| | C | H | F |
|---|---|---|---|
| | | | (unit: % by weight) |

Figure 3:
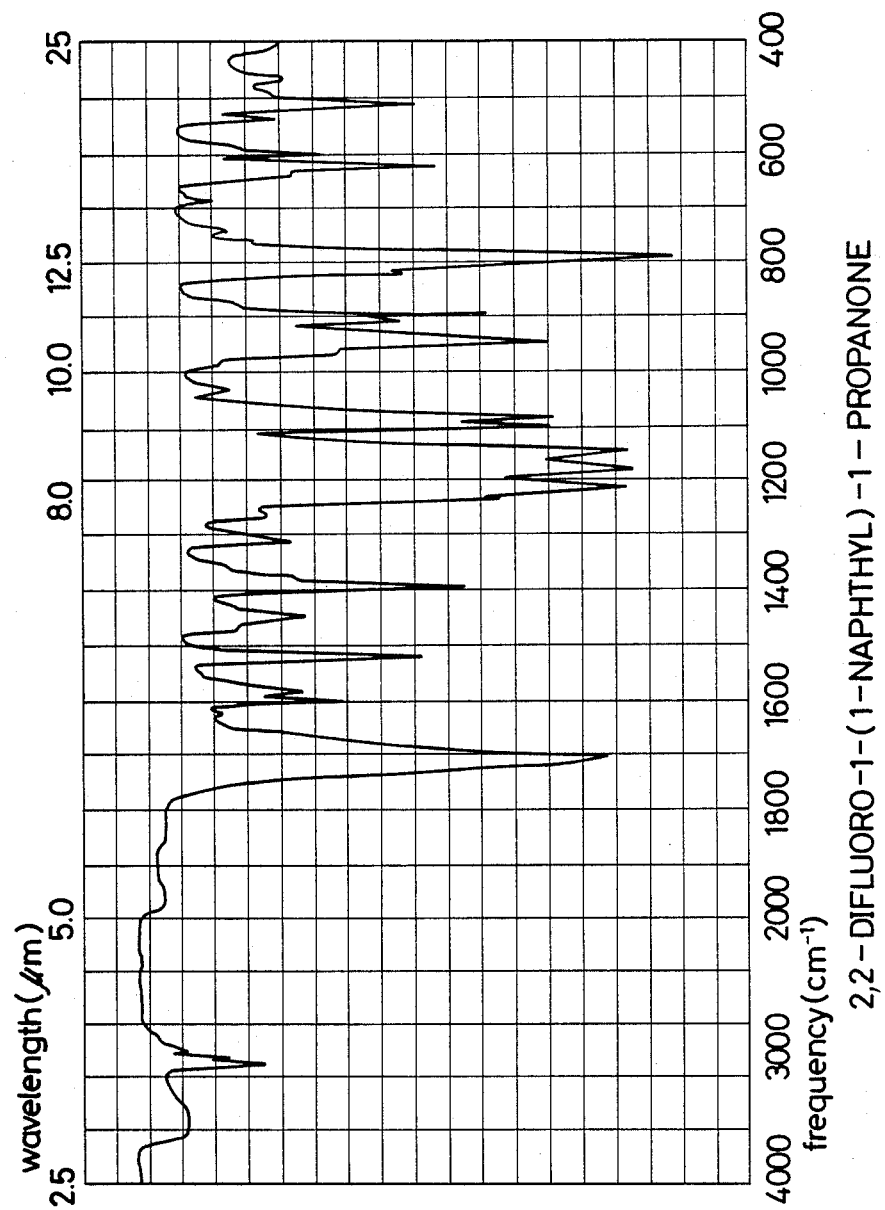
Figure 4:
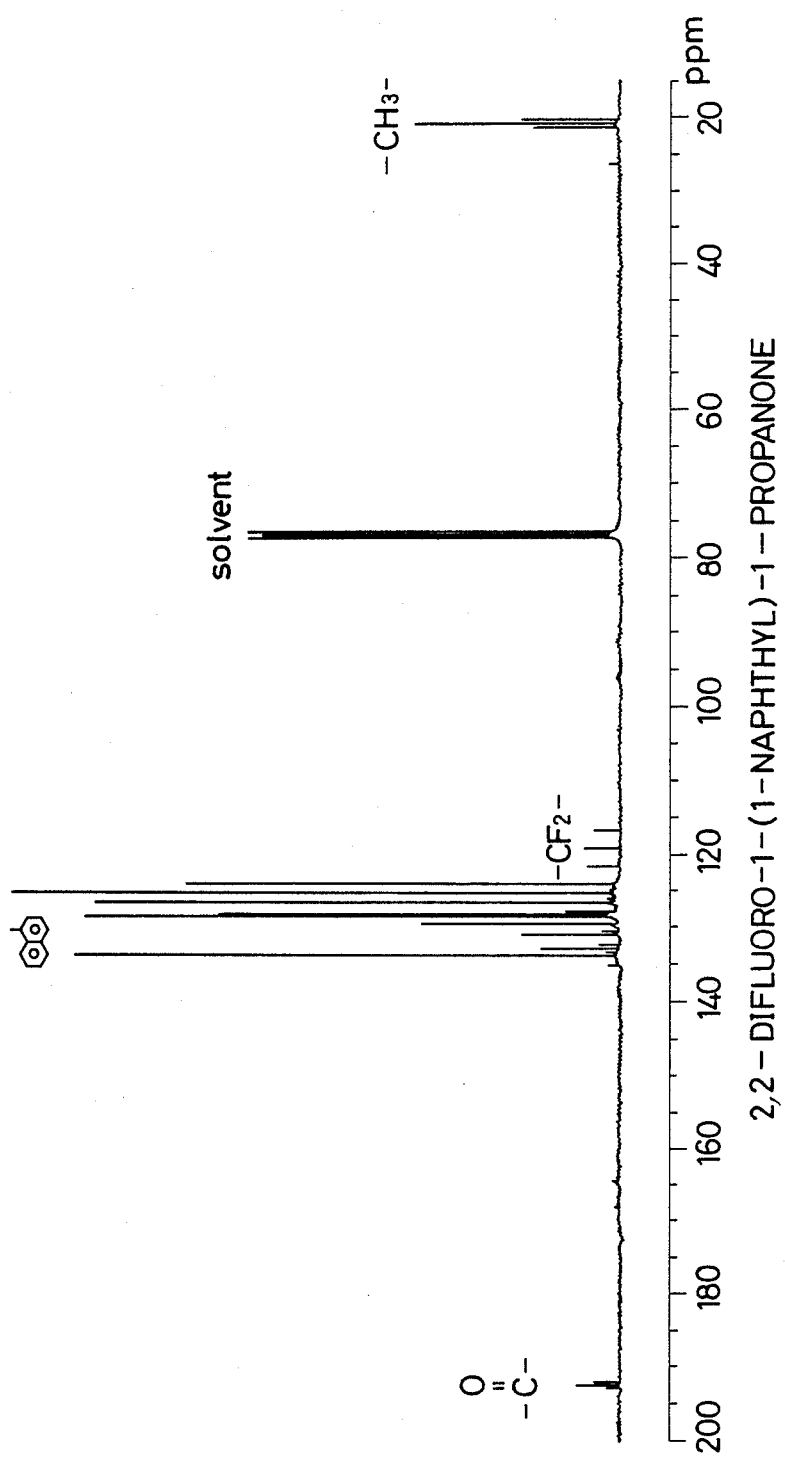

EIMS mass spectrometry of the distillate showe a maximum peak at 155 (—$C_{10}H_7CO$—) and peaks at 127 (—$C_{10}H_7$—) and at 220 (molecular weight). IR and $^{13}C$-NMR analyses were also made with the spectra shown in FIGS. 3 and 4.

As evidenced by the various analyses, the distillate was identified as 2,2-difluoro-1-(1-naphthyl)-1-propanone according to the invention.

EXAMPLE 3

Fluorinated naphthylpropanone of Example 2 was evaluated with respect to its insulation characteristics.

The compound was blended in varying amounts with a base oil (Condenser Oil S, Nippon Oil Co., Ltd.) to provide different insulating oils. Dry alumina was put into the oils in an amount of 5 g per 100 g of the oil and passed through a 0.2 m perforated Teflon filter, followed by admixture with 3 g of molecular sieve 5A and by subsequent filtration on a similar filter, thereby obtaining refined oil samples.

The test oils were measured for electrical and physical properties with the results tabulated.

The oils embodying the invention have proved highly satisfactory in respect of all the characteristics tested. Control oil (unblended base oil) was insufficient in dielectric constant, hydrogen gas adsorptivity, pour point and viscosity.

TABLE

| additive (wt. %)*[1] | 0 | 15 | 20 |
|---|---|---|---|
| dielectric constant ($\epsilon$, 80 C.) | 2.53 | 3.74 | 4.12 |
| dielectric loss (tan $\delta$, %, 80 C.) | 0.04 | 0.16 | 0.27 |
| hydrogen gas absorptivity*[2] | 230 | 260 | 275 |
| pour point | −45 | −50 | −50 |
| viscosity (cSt) | | | |
| 40° C. | 4.90 | 4.22 | 4.08 |
| 0° C. | 23.3 | 15.6 | 13.9 |
| −30° C. | 160 | 148 | 138 |

Notes:
*[1]fluorinated naphthylpropanone of Example 2, based on total weight of oil composition
*[2]—$\Delta H_2$ mmHg/100 min, electrode gap 10 mm, 8 KV, by the procedure disclosed for instance in "Kogyo Kagaku Zasshi" (Journal of Industrial Chemistry), vol. 64. no. 9, page 1553 (1961), Japan

What is claimed is:

1. A naphthalene derivative of the formula

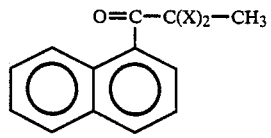

where X is a fluorine or bromine atom.

2. 2,2-Difluoro-1-(1-naphthyl)-1-propanone.
3. 2,2-Dibromo-1-(1-naphthyl)-1-propanone.
4. A process for producing a naphthalene derivative of the formula

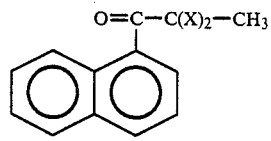

where X is a fluorine or bromine atom, which comprises:
 (a) preparing a mixture of 1-(1-naphthyl)-1propanone and 1-(2-naphthyl)-1-propanone by reaction of naphthalene with propionyl chloride at from 20° to 250° C. and in the presence of a Friedel-Crafts catalyst;
 (b) reacting compound (a) with a brominating agent at from 0° to 80° C. and with or without use of a solvent, thereby giving 2,2-dibromo-1-(1-naphtyl)-1-propanone combined with 2,2-dibromo-1-(2-naphthyl)-1-propanone; and
 (c) subsequently purifying ad isolating compound (b) with use of a solvent, whereby 2,2-dibromo-1-(1-naphthyl)-1-propanone is provided.

5. The process of claim 4 further including a reaction of compound (c) with a fluorinating agent at from 0o to 120° C. and with or without use of a solvent. whereby 2,2-difluoro-1-(1-naphthyl)-1-propanone is provided.

6. The process of claim 4 wherein said catalyst is aluminum chloride or iron chloride.

7. The process of claim 4 wherein said brominating is bromine gas or N-bromosuccinimide.

8. The process of claim 4 wherein said solvent in (b) is carbon tetrachloride, chloroform, dichloroethane, tetrahydrofuran or carbon disulfide.

9. The process of claim 4 wherein said solvent in (c) is pentane, hexane, keptane, octane, methanol, ethanol, propanol or butanol, or a combination thereof.

10. The process of claim 5 wherein said fluorinating agent is fluorine gas, hydrogen fluoride, sulfur fluoride, potassium fluoride, xenon fluoride, mercury fluoride, silver fluoride, antimony fluoride, $CHF_3$, $CF_3OF$, $(C_2H_5)_2NSF_3$, $\phi_4P^+HF_2^-$, or $\phi_3(iso-C_3H_7)P^+HF_2^-$.

11. The process of claim 5 wherein said solvent is carbon tetrachloride, perfluorohexane or perfluorooctane.

12. An insulating oil comprising a base oil and a compound of claim 2.

13. The oil of claim 12 wherein said compound is present in an amount of 5 to 40 percent by weight of the total oil composition.

14. The oil of claim 12 wherein said base oil is selected from the group consisting of mineral oils, hard alkylbenzenes, soft alkylbenzenes, polybutenes, alkylnaphthalenes, diarylalkanes and silicone oils.

* * * * *